(12) United States Patent
Shoji et al.

(10) Patent No.: US 7,909,604 B2
(45) Date of Patent: Mar. 22, 2011

(54) ROOT APEX POSITION DETECTION APPARATUS

(75) Inventors: Shigeru Shoji, Sendai (JP); Masahiro Otsuka, Kawasaki (JP)

(73) Assignee: Toei Electric Co., Ltd., Kanagawa (JP)

( * ) Notice: Subject to any disclaimer, the term of this patent is extended or adjusted under 35 U.S.C. 154(b) by 0 days.

(21) Appl. No.: 11/297,993

(22) Filed: Dec. 9, 2005

(65) Prior Publication Data

US 2006/0093986 A1    May 4, 2006

Related U.S. Application Data

(63) Continuation of application No. PCT/JP2004/007046, filed on May 18, 2004.

(30) Foreign Application Priority Data

Jun. 11, 2003    (JP) .................................. 2003-167008

(51) Int. Cl.
*A61C 19/04*    (2006.01)
*A61B 5/05*    (2006.01)
*A61B 5/103*    (2006.01)

(52) U.S. Cl. ............. 433/72; 433/32; 600/547; 600/590

(58) Field of Classification Search .................... 433/72, 433/75, 27, 28, 32; 600/590, 547
See application file for complete search history.

(56) References Cited

U.S. PATENT DOCUMENTS

| | | | | |
|---|---|---|---|---|
| 3,753,434 A | * | 8/1973 | Pike et al. | 433/32 |
| 3,916,529 A | * | 11/1975 | Mousseau | 600/547 |
| 4,353,693 A | * | 10/1982 | Dery et al. | 433/27 |
| 4,447,206 A | * | 5/1984 | Ushiyama | 433/27 |
| 5,017,134 A | * | 5/1991 | Saito et al. | 433/72 |
| 5,096,419 A | | 3/1992 | Kobayashi et al. | |
| 5,112,224 A | * | 5/1992 | Shirota | 433/27 |
| 5,211,556 A | * | 5/1993 | Kobayashi et al. | 433/72 |
| 5,759,159 A | * | 6/1998 | Masreliez | 600/547 |

(Continued)

FOREIGN PATENT DOCUMENTS

JP    7-275263    10/1995

(Continued)

OTHER PUBLICATIONS

International Preliminary Report on Patentability, PCT/JP2004/007046, issued Apr. 24, 2006.

*Primary Examiner* — Cris L Rodriguez
*Assistant Examiner* — Michael R Ballinger
(74) *Attorney, Agent, or Firm* — Michael Best & Friedrich LLP (57) ABSTRACT

Root apex position model data associated with electrical characteristic values between a measurement electrode and a mouth electrode in a state in which the distal end of the measurement electrode is located at a root apex position of a root canal is stored in a storage unit. A power supply applies measurement signals of 500 Hz and 2 kHz between the measurement electrode and the mouth electrode. Two different current values flowing between the measurement electrode and the mouth electrode are detected. These current values are compared with the root apex position mode data stored in the storage unit. If the root apex position data includes any data which coincides with the current values, it is detected that the distal end of the measurement electrode is located at the root apex position.

2 Claims, 9 Drawing Sheets

U.S. PATENT DOCUMENTS

| | | | |
|---|---|---|---|
| 6,059,569 A | 5/2000 | Otsuka | |
| 6,221,031 B1 * | 4/2001 | Heraud | 600/547 |
| 6,425,875 B1 * | 7/2002 | Reifman et al. | 600/590 |
| 6,501,542 B2 * | 12/2002 | Jung et al. | 356/73 |
| 6,845,265 B2 * | 1/2005 | Thacker | 600/547 |
| 6,968,229 B2 * | 11/2005 | Siemons | 600/547 |
| 2004/0019291 A1 * | 1/2004 | Thacker | 600/547 |
| 2004/0225234 A1 * | 11/2004 | Siemons | 600/590 |

FOREIGN PATENT DOCUMENTS

| | | |
|---|---|---|
| JP | 2000-5201 | 1/2000 |
| JP | 2000-60878 | 2/2000 |

* cited by examiner

ROOT APEX POSITION DETECTION APPARATUS

CROSS REFERENCE TO RELATED APPLICATIONS

This is a Continuation Application of PCT Application No. PCT/JP2004/007046, filed May 18, 2004, which was published under PCT Article 21(2) in Japanese.

This application is based upon and claims the benefit of priority from prior Japanese Patent Application No. 2003-167008, filed Jun. 11, 2003, the entire contents of which are incorporated herein by reference.

BACKGROUND OF THE INVENTION

1. Field of the Invention

The present invention relates to a root apex position detection apparatus which is used to measure root canal length in dental diagnosis and treatment.

2. Description of the Related Art

When treating a tooth, a dentist sometimes needs to remove the dental pulp and nerve in the root canal. In this case, the dentist measures a distance between the tooth crown and the root apex and removes the dental pulp and nerve in the root canal by an amount corresponding to the distance or infected dentin or foreign bodies in the root canal. For distance measurement, a root apex position detection apparatus is used. In using the root apex position apparatus, a mouth electrode is placed in oral cavity, and a measurement electrode is inserted into the root canal. An AC signal is then applied between the measurement electrode and the mouth electrode, and the root apex position is detected in accordance with the value of a signal (electrical characteristic value) measured when the measurement electrode reaches the root apex position.

By monitoring that the indicator of a display unit indicates a predetermined position, the dentist knows that the measurement electrode has reached the root apex.

It is important for treatment in the root apex to accurately detect the root apex position of the tooth. If the root apex position is not accurately detected, the above distance will contain an error. If the dentist performs treatment trusting the distance containing the error, the dental pulp and nerve or infected dentin or foreign bodies may be left in the root canal, or the dentist may damage the root apex during operation.

The state inside the root canal of the tooth to be treated varies, case by case, from a dry state in which the interior of the root canal is dry to a wet state in which the interior of the root canal is filled with blood or the like. A conventional root canal length measurement apparatus can accurately detect the root apex position if the state inside the root canal of the tooth satisfies predetermined conditions (thickness, shape (arcuation or bifurcation), and the degree of dryness/wetness). If, however, the state inside the root canal of the tooth does not satisfy the specific conditions, the measured value contains an error.

A mark indicating the root apex position and marks adjacent to the root apex position are formed on a scale mark on the display of the conventional root apex position detection apparatus. If the state inside the root canal satisfies the specific conditions as described above, the scale mark can accurately indicate that the measurement electrode is located at the root apex position. However, the marks adjacent to the root apex position only indicate that the measurement electrode is located around the root apex position, but cannot indicate how far the measurement electrode is away from the root apex position.

In addition, before measuring the root canal length with a conventional root canal length measurement instrument, it is necessary to match a position of a silicone stopper inserted in a reamer or file to the root canal length by using a radiograph. Even if a mark is made by the silicone stopper added to the reamer or file or the silicone stopper added to the reamer or file which has once determined the root canal length, the silicone stopper is shifted, and an accurate length cannot be displayed in some cases. When the mark is hidden behind the tooth and cannot be recognized on a radiograph, the measurement operation must be stopped halfway.

BRIEF SUMMARY OF THE INVENTION

It is an object of the invention of the present application to solve at least one of the problems in the prior art described above.

According to a first aspect of the invention of the present application, there is provided a root apex position detection apparatus for detecting a root apex position of a root canal of a test tooth. This root apex position detection apparatus comprises:

a measurement electrode which is inserted into the root canal;

a mouth electrode which is placed on an intraoral surface;

a power supply which applies a plurality of types of measurement signals to one of the measurement electrode and the mouth electrode;

a storage unit to store root apex position model data, the root apex position model data having a plurality of model tooth data groups, each of the model tooth data groups comprising electrical characteristic values between the measurement electrode and the mouth electrode with respect to each of the plurality of types of measurement signal while a distal end of the measurement electrode is placed at a root apex position of a model tooth, and the model tooth including different model teeth for each model tooth data group;

a detection unit which sequentially detects a plurality of electrical characteristic values between the measurement electrode and the mouth electrode on the basis of each measurement signal, in the process of inserting the measurement electrode into the root canal toward the root apex position, while sequentially applying each of the plurality of types of measurement signals to one of the measurement electrode and the mouth electrode;

a comparison unit (12) which compares the test tooth data group comprising the plurality of electrical characteristic values sequentially detected by the detection unit with the plurality of the model tooth data groups in the root apex position model data stored in the storage unit, detects that there is a model tooth data group in a predetermined relationship with the test tooth data group, and outputs a detected result; and a display unit to display the detected result output from the comparison unit.

According to a second aspect of the invention of the present application, there is provided a root apex position detection apparatus for detecting a root apex position of a test tooth and a distance between a distal end of a measurement electrode and the root apex position. This root apex position detection apparatus comprises:

a measurement electrode which is inserted into the root canal;

a mouth electrode which is placed on an intraoral surface;

a power supply which applies a plurality of types of measurement signals to one of the measurement electrode and the mouth electrode;

a storage unit which stores intra-root-canal-position-specific model data, the intra-root-canal-position-specific model data comprising a plurality of model tooth data groups, each of the model tooth data groups comprising electrical characteristic values between the measurement electrode and the mouth electrode with respect to a plurality of types of measurement signals in a state in which the distal end of the measurement electrode is located at each of a plurality of predetermined positions in a model tooth, and the model tooth including different model teeth for each model tooth data group;

a detection unit which sequentially detects a plurality of electrical characteristic values between the measurement electrode and the mouth electrode with respect to each of the plurality of types of measurement signals in the process of applying each of the plurality of measurement signals to one of the measurement electrode and the mouth electrode and inserting the distal end of the measurement electrode from a root canal orifice of the test tooth to the root apex position; and a comparison unit which compares the test tooth data group comprising the plurality of electrical characteristic values sequentially detected by the detection unit with the plurality of the model tooth data groups in the intra-root-canal-position-specific model data stored in the storage unit, detects that there is a model tooth data group in a predetermined relationship with the test data group, and outputs a detected result as a position information.

Each of the root apex position detection apparatuses based on the first and second aspects of the invention of the present application preferably comprises one of a) to g) described below or a combination thereof.

(a) The plurality of types of measurement signals differ from each other in at least one of frequency, waveform, and peak value.

(b) The plurality of types of measurement signals comprise two types of measurement signals, the two types of measurement signals having voltages which differ from each other in frequency.

(c) The electrical characteristic value detected by the detection unit is at least one of an impedance value between the two electrodes, a current value flowing between the two electrodes, a voltage value between the two electrodes, and a phase difference between the current value or voltage value between the two electrodes and the measurement signal.

(d) The predetermined relationship detected by the comparison unit is at least one of a relationship in which the test tooth data group coincides with any one of the plurality of the model tooth data groups in the root apex position model data stored in the storage unit and a relationship in which a difference between the test tooth data group and the model tooth data group falls within a predetermined range.

(e) The detected result output from the comparison unit is used for at least one of display, warning, and control on a dental instrument.

(f) The root apex position model data is one of measured data based on an actual tooth, theoretical data, simulation data, approximate data obtained by calculation based on measured data, and data obtained combining at least two thereof.

(g) A display unit to display the detected result output from the comparison unit.

According to a third aspect of the invention of the present application, the root apex position detection apparatus according to the second aspect further comprises: a storage unit which stores predictive intra-root-canal-position-specific model data together with the intra-root-canal-position-specific model data, the predictive intra-root-canal-position-specific model data having an electrical characteristic value predicted at a position midway between one predetermined position of a plurality of predetermined positions and the next predetermined position; and a comparison unit which compares a measured electrical characteristic value sequentially detected by the detection unit with the intra-root-canal-position-specific model data and the predictive intra-root-canal-position-specific model data stored in the storage unit, detects that the two model data include data in a predetermined relationship with the measured electrical characteristic value, and outputs a detected result.

The root apex position detection apparatus based on the third aspect of the invention of the present application preferably comprises one of h) to t) described below or a combination of thereof.

(h) A display unit to display the detected result output from the comparison unit.

(i) The plurality of types of measurement signals differ from each other in at least one of frequency, waveform, and peak value.

(j) The plurality of types of measurement signals comprise two types of measurement signals, the two types of measurement signals having voltages which differ from each other in frequency.

(k) The electrical characteristic value detected by the detection unit is at least one of an impedance value between the two electrodes, a current value flowing between the two electrodes, a voltage value between the two electrodes, and a phase difference between the current value or voltage value between the two electrodes and the measurement signal.

(l) The predetermined relationship detected by the comparison unit is at least one of a relationship in which the test tooth data group coincides with any one of the plurality of model tooth data groups in the intra-root-canal-position-specific model data stored in the storage unit and a relationship in which a difference between the test tooth data group and the model tooth data group falls within a predetermined range.

(m) The detected result output from the comparison unit is used for at least one of display, warning, and control on a dental instrument.

(n) The root apex position model data is one of measured data based on an actual tooth, theoretical data, simulation data, approximate data obtained by calculation based on measured data, and data obtained combining at least two thereof.

(o) An electrical characteristic value at least one position midway between an intra-root-canal position indicated by the detected result output from the comparison unit and the next intra-root-canal position is predicted by a prediction unit, wherein, the electrical characteristic value predicted by the prediction unit is a predicted electrical characteristic value.

(p) The plurality of types of measurement signals comprise two types of measurement signals, the two types of measurement signals having voltages which differ from each other in frequency.

(q) The electrical characteristic value detected by the detection unit is at least one of an impedance value between the two electrodes, a current value flowing between the two electrodes, a voltage value between the two electrodes, and a phase difference between the current value or voltage value between the two electrodes and the measurement signal.

(r) The predetermined relationship detected by the comparison unit is at least one of a relationship in which the test tooth data group coincides with any one of a plurality of model tooth data groups in the intra-root-canal-position-specific model data stored in the storage unit and a relationship in which a difference between the test tooth data group and the model tooth data group falls within a predetermined range.

(s) The detected result output from the comparison unit is used for at least one of display, warning, and control on a dental instrument.

(t) The root apex position model data is one of measured data based on an actual tooth, theoretical data, simulation data, approximate data obtained by calculation based on measured data, and data obtained combining at least two thereof.

DETAILED DESCRIPTION OF THE INVENTION

The first embodiment of the present invention will be described below with reference to the views of the accompanying drawing.

Figure 1:
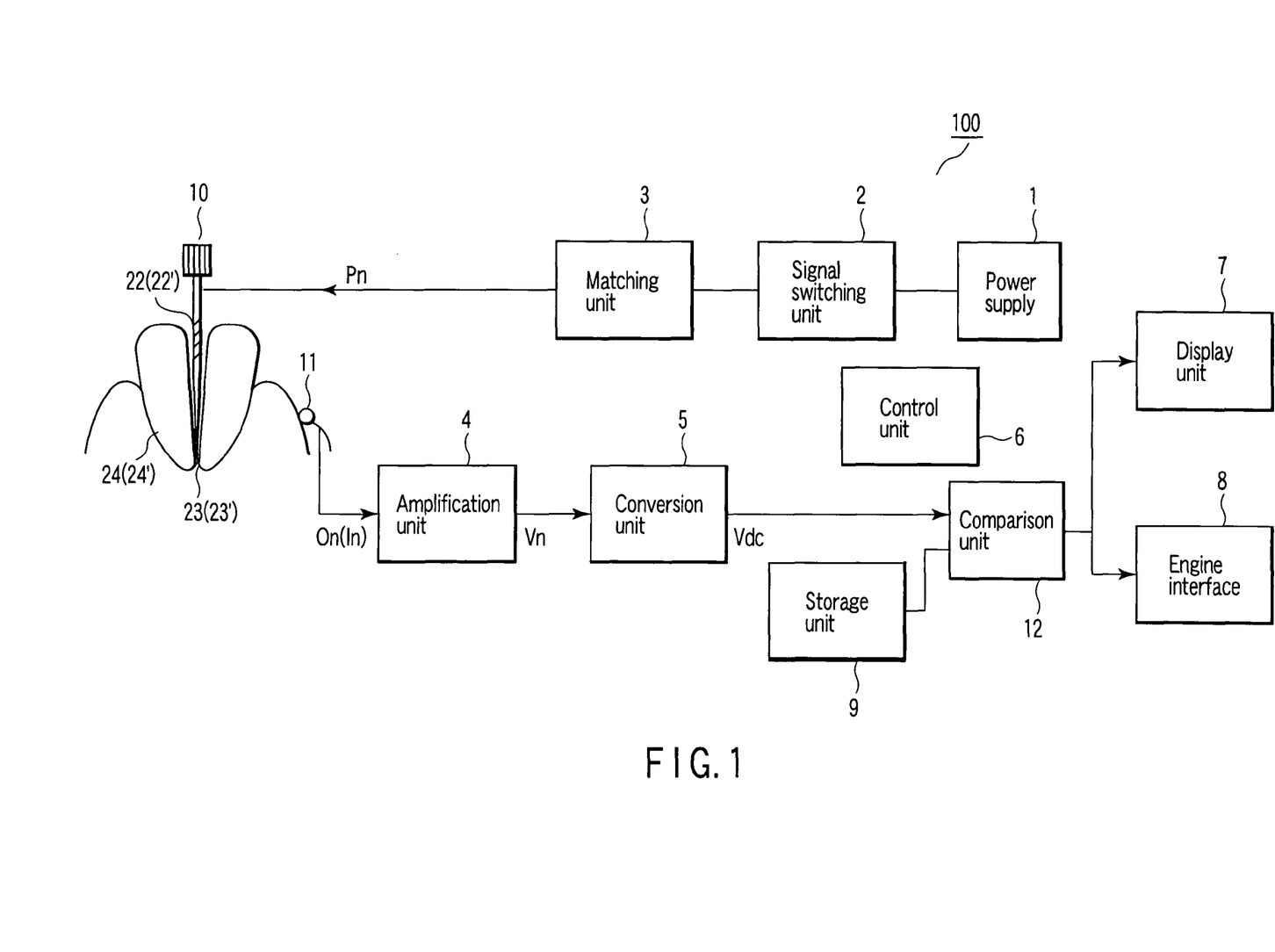
FIG. 1 is a view showing one embodiment of a root apex detection apparatus of the invention of the present application.

Referring to FIG. 1, a power supply 1 outputs a plurality of types of measurement signals Pn. The measurement signals Pn can be signals of two different frequencies of, e.g., 500 Hz and 2 kHz. The measurement signals Pn can be signals of three or more types of frequencies. The measurement signals Pn can be signals which differ from each other in at least one of frequency, waveform, or peak value. According to the invention of the present application, it is necessary to detect a plurality of types of electrical characteristic values between a measurement electrode 10 and a mouth electrode 11 on the basis of a plurality of types of measurement signals Pn, and the types of the signals can be selected on the basis of the principle of the invention of the present application to be described below.

In addition, although the measurement signals Pn are applied to the measurement electrode 10, the signals may be applied to the mouth electrode 11.

For the sake of a more detailed description of this embodiment, the embodiment will exemplify a case wherein signals of two different frequencies, namely 500 Hz and 2 kHz, are used as the measurement signals Pn, and the measurement signals are applied to the measurement electrode. However, the invention of the present application is not limited to this case.

The power supply 1 outputs the measurement signals of two different frequencies, namely 500 Hz and 2 kHz.

A signal switching unit 2 sequentially supplies the measurement signals of the two different frequencies, i.e., 500 Hz and 2 kHz, output from the power supply 1 to the measurement electrode under the control of a control unit 6. As the signal switching unit 2, a switching unit such as a so-called multiplexer or the like can be used.

A matching unit 3 is a portion which converts a signal from the signal switching unit into a signal with a voltage level at which the signal can be safely applied to the human body, and prevents a measurement current from needlessly flowing in the human body. The matching unit 3 adjusts the measurement signals Pn from the power supply 1 to signals suitable for being supplied to the measurement electrode 10. If, however, the measurement signals Pn from the power supply are signals suitable for being applied to the measurement electrode 10, the matching unit 3 can be omitted. In this embodiment, the matching unit 3 adjusts the measurement signals Pn of the two different frequencies, i.e., 500 Hz and 2 kHz, to a predetermined voltage value Vn.

An amplification unit 4 connected to the mouth electrode 11 amplifies a measured signal Qn output from the mouth electrode 11. The measured signal Qn is a value associated with an electrical characteristic value between the measurement electrode 10 and the mouth electrode 11. The electrical characteristic value can be any one of a current value In flowing between the two electrodes (to be referred to as a "measured current value In" hereinafter), the voltage value Vn between the two electrodes (to be referred to as the "measured voltage value Vn" hereinafter), a phase difference between the current value In and the measurement signal Pn, a phase difference between the voltage value Vn and the measurement signal Pn, and an impedance value Zn between the two electrodes (to be referred to as an "intra-root-canal impedance value Zn" hereinafter), or a combination of these tooth data groups.

These electrical characteristic values can also be obtained from the measured signal Qn itself or by combining it with other signal values.

An electrical characteristic value in the invention of the present application is not limited to the measured current In. For the sake of a more detailed description of this embodiment, however, a case wherein the electrical characteristic value is the measured current In will be described.

The amplification unit 4 converts the measured current In into a voltage and amplifies the voltage, and a known amplifier can be used.

A conversion unit 5 is a circuit which converts a measured AC voltage Vn amplified by the amplification unit 4 into a DC voltage Vdc which can be read and stored by the control unit.

The control unit 6 controls predetermined devices in a root apex position detection apparatus 100 according to this embodiment.

In this embodiment, a detection unit 25 comprises the power supply 1, signal switching unit 2, matching unit 3, measurement electrode 10, mouth electrode 11, amplification unit 4, conversion unit 5, and control unit 6. The detection unit 25 can employ any arrangement as long as it can detect electrical characteristics of a tooth located between the measurement electrode and the mouth electrode. The detection unit 25 applies each of the measurement signals Pn of the two different frequencies, i.e., 500 Hz and 2 kHz, to the single measurement electrode 10, and detects two types of electrical characteristic values between the measurement electrode 10 and the mouth electrode 11 which are based on the respective measurement signals.

In this embodiment, the control unit 6 controls predetermined devices in the root apex position detection apparatus 100, and can also execute control to compare a plurality of model tooth data groups of root apex position model data associated with electrical characteristic values stored in a storage unit 9 with a test tooth data group having electrical characteristic values of a test tooth 24 to be treated which are detected by the detection unit 25 so as to check whether or not there is any model tooth data group which is in a predetermined relationship with the test tooth data group.

The storage unit 9 stores the root apex position model data associated with the electrical characteristic value In between the measurement electrode 10 and the mouth electrode 11 while the distal end of the measurement electrode 10 is located at a root apex position 23' of a root canal 22' of a model tooth 24'. The model teeth 24' are sample teeth which differ from each other in root canal structure or the state inside the root canal (the degree of wetness ranging from that in the dry state to that in the wet state). This root apex position model data has a plurality of tooth data groups comprising two types of electrical characteristic values obtained when the measured signals Vn of the two different frequencies, i.e., 500 Hz and 2 kHz, are applied to the model tooth 24'.

The respective groups can use measured data obtained from different actual sample teeth as targets. The measured data of each model tooth data group can be the electrical characteristic values In between the measurement electrode 10 and the mouth electrode 11 which are obtained by applying the two types of measurement signals Pn of 500 Hz and 2 kHz while the distal end of the measurement electrode 10 is located at a root apex position 23 of the predetermined model tooth 24'.

Figure 2:
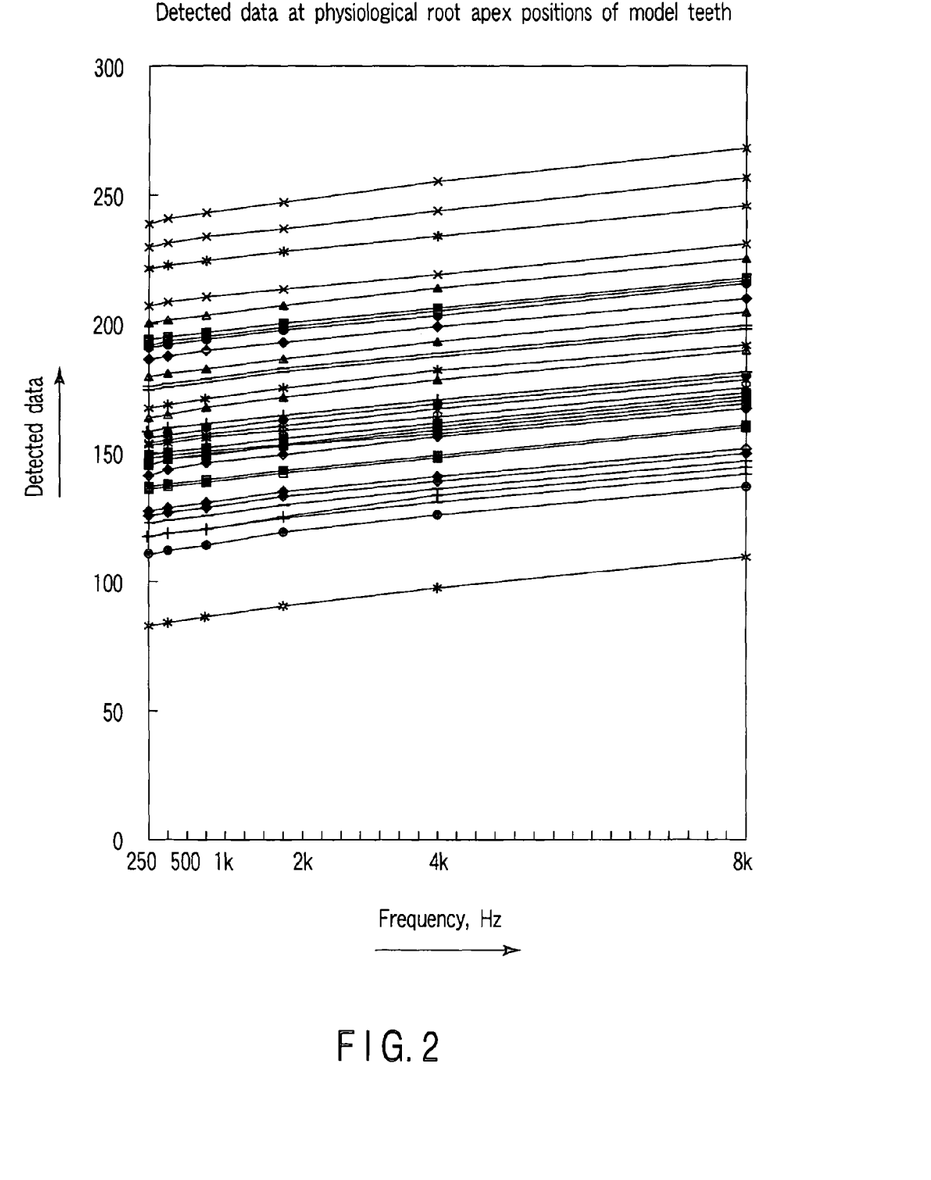
FIG. 2 is a graph showing a relation between frequencies of measurement signals applied to a measurement electrode at a root apex position of each of a plurality of model teeth and measured data of current values flowing between the measurement electrode and a mouth electrode.

The measured data at this root apex position (physiological root apex position) will be described in more detail with reference to FIG. 2. Referring to FIG. 2, the ordinate represents the (quantified) measured current In; and the abscissa, the frequency of a measurement signal. FIG. 2 shows a relationship between the measured current In and a frequency f in a state wherein the distal end of the measurement electrode 10 is located at the root apex position. One line represents data associated with one model tooth 24'. In this case, even one model tooth 24' having the same root canal structure is considered as a different model tooth 24' if the state inside the root canal (e.g., the degree of a dry state or wet state or a change in thickness) is different.

This measured data was obtained by using Justy II (trade name) available from Toei Electric Co., Ltd as a root apex position detection apparatus upon partly modifying it. With this modification, the frequencies of measurement signals of 500 Hz and 2,000 Hz could be set in the range of 250 to 8,000 Hz. The output current of a detection output from the Justy II was supplied to a detection resistor, and a voltage across the resistor was used as measured data. Measurement targets were those from whom informed concept was obtained.

FIG. 2 shows the measured data of the model teeth 24' in about 30 cases. In FIG. 2, when perpendiculars are dropped at the positions of frequencies of 500 Hz and 2 kHz, the model tooth data group with the value of the intersection of each perpendicular and measured data for each model tooth 24' can be obtained. Referring to FIG. 2, the model tooth data groups of the values of the intersections associated with the model teeth 24' in about 50 cases can be obtained. Readings at 500 Hz indicate variation of about 70 to 280.

As described above, the ordinate data (electrical characterized values) of the respective model teeth 24' do not indicate any constant value. That is, it can be understood that the respective teeth have unique electrical characteristic values.

Figure 3:
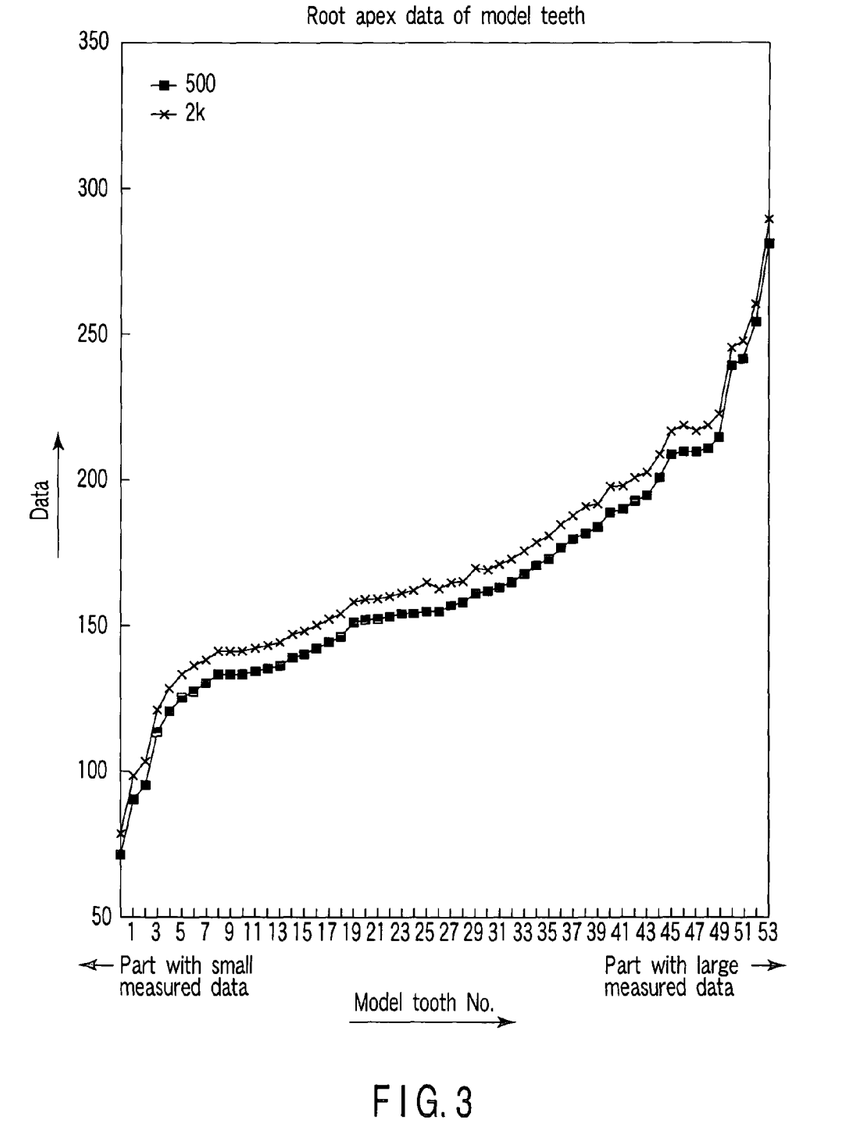
FIG. 3 is a cumulative plot of the current value flowing between the measurement electrode and the mouth electrode with respect to the measurement signals of 500 Hz and 2 kHz based on the measured data in FIG. 2.

Referring to FIG. 3, the model tooth data groups of the values of the intersections associated with the model teeth 24' in about 50 cases shown in FIG. 2 are rearranged in the order of the measured data.

Referring to FIG. 3, the data indicated on the ordinate are quantified values, the data marked with the crosses represent the values of measured data at the measurement signal Pn of 2 kHz, and the data marked with "■" represent the values of measured data at the measurement signal Pn of 500 Hz. For each sample, data corresponding to the two measurement signals form one model tooth data group.

As is obvious from FIG. 3, about 50 model tooth data groups which are obtained from the different model teeth 24' can be obtained as root apex position model data to be stored in the storage unit 9.

A comparison unit 12 compares the test tooth data groups of the two types of electrical characteristic values In associated with the test tooth 24 to be treated, which are detected by the detection unit 25, with the values of the model tooth data groups in the root apex position model data stored in the storage unit 9 to check whether or not the root apex position model data includes any model tooth data group having a predetermined relationship with the test tooth data group. The test result obtained by the comparison unit 12 is sent as position information associated with the position of the measurement electrode to a display unit 7. The above-described "predetermined relationship" can be a relationship in which the test tooth data group comprising the two types of electrical characteristic values detected by the detection unit coincides with any model tooth data group in the root apex position model tooth data stored in the storage unit. Alternatively, the above-predetermined relationship may be a relationship in which the difference between the test tooth data group and the model tooth data group falls within a predetermined range. This range can be set to 5%.

The display unit 7 displays the output from the comparison unit 12 as the detected result obtained by the root apex position detection apparatus 100. That is, upon receiving information indicating "coincidence" from the comparison unit 12, the display unit 7 displays information indicating that the distal end of the measurement electrode is located at the root apex position 23. Upon receiving information indicating "incoincidence" from the comparison unit 12, the display unit 7 displays information indicating that the distal end of the measurement electrode is not located at the root apex position 23.

As the display unit 7, any unit which can inform the dentist of a root apex position, e.g., an analog meter, a digital meter, a unit which produces a sound (e.g., a warning sound), a unit which emits light (e.g., warning light), or a unit which produces vibrations, can be used.

In the first embodiment, an output from the comparison unit 12 is sent to the display unit 7. The output from the comparison unit 7 can also be used as an output for warning.

In this case, the output from the comparison unit 7 can be used to inform that the distal end of the measurement electrode 10 is located at the root apex position 23, by using sound, light, vibrations, or the like. The output from the comparison unit 7 can be used to control a dental instrument (e.g., an automatic root canal expanding instrument with a dental electric engine).

An interface unit 8 is a circuit for supplying an output from the comparison unit 12 to the automatic root canal expanding tool with the dental electric engine. The automatic root canal expanding instrument can mechanically execute root canal expanding operation, instead of manual root canal expanding operation by the dentist, by using a reamer and file which are rotated by the dental electric engine controlled on the basis of data from the root canal length measurement instrument.

The operation of the root apex position detection apparatus according to the first embodiment of the invention of the present application will be described.

(1) Root apex position model data associated with electrical characteristic values between the measurement electrode and the mouth electrode in a state wherein the distal end of the measurement electrode 10 is located at the root apex position 23 of the root canal is stored in the storage unit 9. This root apex position model data is current values (electrical characteristic values) flowing between the two electrodes when measurement signals of the two different frequencies, i.e., 500 Hz and 2 kHz, are applied to the measurement electrode 10 while the distal end of the measurement electrode 10 is located at the root apex position 23' of the root canal 22' of the model tooth 24'. It is preferable to store model data about more model teeth 24'.

(2) The mouth electrode 11 is brought into contact with the oral cavity having the test tooth 24, and the measurement electrode 10 is located at a measurement start position (e.g., a tooth crown portion) in the root canal of the tooth.

(3) The measurement signals Pn of the two different frequencies, i.e., 500 Hz and 2 kHz, are sequentially supplied from the power supply 1 to the measurement electrode while the measurement electrode 10 is moved toward the root apex position 23. Alternatively, the supply of the measurement signals of the two different frequencies, i.e., 500 Hz and 2 kHz, from the power supply 1 to the two electrodes can be started before the measurement electrode 10 starts to move toward the root apex position 23.

(4) The signal switching unit 2 adjusts the supply timing of each measurement signal Pn so as to sequentially supply the measurement signals Pn of the two different frequencies, i.e., 500 Hz and 2 kHz, from the power supply 1 to the measurement electrode.

(5) Two types of electrical characteristic values (current values In in this case) between the two electrodes are output from the mouth electrode 11 on the basis of the measurement signals Pn of 500 Hz and 2 kHz sequentially supplied from the signal switching unit 2 to the measurement electrode.

(6) Each of the current values In representing these two types of electrical characteristic values is converted into a voltage value and amplified by the amplification unit 4.

(7) Each of the two different amplified voltage values Vn is converted into the DC voltage value Vdc by the conversion unit 5.

(8) The comparison unit 12 compares the test tooth data group comprising the two different DC voltage values Vdc output from the conversion unit 5 with a plurality of model tooth data groups in the root apex position model data stored in the storage unit 9 to check whether or not the test tooth data group comprising the two different DC voltage values Vdc coincides with any one of the plurality of model tooth data groups in the root apex position model data.

(9) The test result obtained by the storage unit 9 is sent to the display unit 7 and displayed on the display unit 7.

The second embodiment of the invention of the present application will be described next. The second embodiment is the same as the first embodiment in the mechanism of detecting a root apex position. The second embodiment differs from the first embodiment in that it detects a distance from a distal end of a measurement electrode 10 to a root apex position 23 as well as the root apex position.

The second measurement differs from the first embodiment in the contents of data stored in a storage unit 9. Intra-root-canal-position-specific model data are stored in the storage unit 9.

It can be understood from the data shown in FIG. 2 that the ordinate data at the root apex positions of a plurality of teeth do not exhibit any constant value.

Likewise, it can be understood that the test tooth data group of two types of electrical characteristic values with respect to measurement signals of 500 Hz and 2 kHz at a predetermined distance from the root apex position differs for each tooth and does not exhibit any constant value.

Intra-root-canal-position-specific model data are data (FIGS. 6, 7, and 2) associated with electrical characteristic values Rn between the measurement electrode 10 and a mouth electrode 11 at each distance from the measurement electrode 10 to a root apex position 23' in the process of inserting the measurement electrode 10 being inserted into a root canal 22' of a model tooth 24' toward the root apex position 23'. That is, the intra-root-canal-position-specific model data are the electric characteristic values Rn between the two electrodes by the distance from the measurement electrode 10 to the root apex position 23'. More specifically, the intra-root-canal-position-specific model data are the two types of electrical characteristic values Rn obtained by applying measurement signals of 500 Hz and 2 kHz to the measurement electrode 10 placed at each of a plurality of model teeth 24'. The more the number of model teeth 24', the better.

The function of a comparison unit 12 is also different from that in the first embodiment. The comparison unit 12 in the second embodiment has the same comparing/checking function for detecting a root apex position as that in the first embodiment. In addition to the function, the comparison unit 12 in the second embodiment has a second function of outputting a test result indicating how far a distal end of the measurement electrode 10 is away from the root apex position.

The second function will be described below. Referring to FIG. 1, in the process of the distal end of the measurement electrode 10 being inserted into the root canal 22', the power supply 1 supplies measurement signals of 500 Hz and 2 kHz to the measurement electrode 10. As a consequence, as the distal end of the measurement electrode 10 is inserted into the root canal 22', the electrical characteristic value Rn between the two electrodes changes.

The comparison unit 12 compares this changing electrical characteristic value (i.e., the two types of electrical characteristic values Rn between the two electrodes with respect to the measurement signals of 500 Hz and 2 kHz) with a plurality of model tooth data groups in the intra-root-canal-position-specific model data stored in the storage unit to detect a model tooth data group which coincides with the changing electrical characteristic value. The comparison unit 12 checks to which position on the model tooth 24' this coincident model tooth data group corresponds, and outputs the corresponding position information to a display unit 7. The display on the display unit 7 allows the dentist to accurately grasp how the measurement electrode 10 approaches the root apex position 23.

As described above, generating the intra-root-canal-position-specific model data of the model tooth 24' at 1-mm distance intervals from the root apex position in this manner makes it possible to detect in a resolution of 1 mm how the distal end of the measurement electrode 10 approaches the root apex position 23'.

By improving the second embodiment, a state wherein the distal end of the measurement electrode 10 approaches the root apex position 23 can be detected more precisely. An example of this improvement is that an intra-root-canal-position-specific model data at least a point between point a1 and point a2 spaced apart by 1 mm is calculated by using an intra-root-canal-position-specific model data at the point a1 and an intra-root-canal-position-specific model data at the point a2 which are stored in the storage unit 9. By using this calculated approximate data as the above intra-root-canal-position-specific model data, the position of the distal end of the measurement electrode 10 can be detected more accurately.

Figure 4:
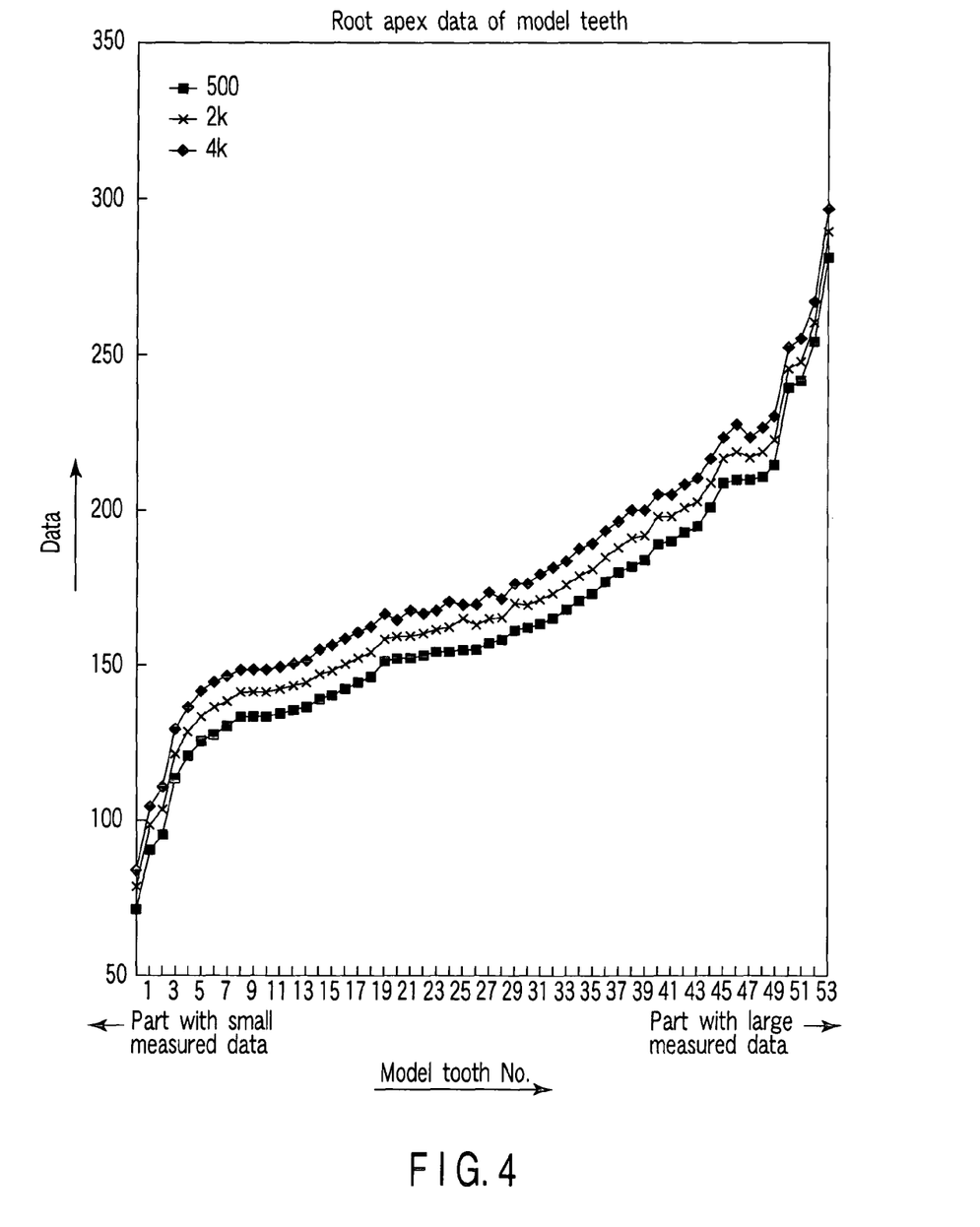
FIG. 4 is a cumulative plot of the current value flowing between the measurement electrode and the mouth electrode with respect to the measurement signals of 500 Hz, 2 kHz, and 4 kHz in increasing order on the basis of the measured data in FIG. 2.

The third embodiment will be described. As shown in FIG. 4, the third embodiment uses three types of data. Referring to FIG. 4, the data indicated on the ordinate are quantified values, the data marked with the crosses represent the values of measured data with a measurement signal Pn of 2 kHz, the data marked with "■" represent the values of measured data with the measurement signal Pn of 500 Hz, and the data marked with "☐" represent the values of measured data with the measurement signal Pn of 4 kHz. An operation of the embodiment using these three types of data is basically the same as in the first and second embodiments described above.

The fourth embodiment will be described. In the first to third embodiments, as root apex position model data, measured data are used. In place of measured data in these embodiments, the third embodiment uses one of theoretical data, simulation data, and approximate data obtained by calculation based on measured data, or data obtained by combining at least two or three of these data, as a root apex position model data or an intra-root-canal-position-specific model data. Where, simulation data is data obtained by, for example, simulation based on tooth models or computer software. Approximate data is data generated from the viewpoint of complementing measured data. For example, in FIG. 2, approximate data is data which satisfies the area without any measured data between the lowest measured data and the measured data immediately above the lowest data. This approximate data can be approximately obtained by using the lowest measured data and the measured data immediately above the lowest data in FIG. 2.

Theoretical data will be described. Based on the root canal structures of various teeth and various intra-root-canal states, the impedance in the root canal changes depending on the root canal structure and the intra-root-canal state. In this case, the intra-root-canal state is a state associated with the degree of wetness from a dry state to a wet state. When the intra-root-canal state of a model tooth 24' having a given root canal structure is changed, the impedance in the root canal which changes can be theoretically calculated.

A substance (e.g., blood) existing in the root canal can be considered as a conductive liquid having a given resistance. Therefore, intra-root-canal impedance values in various intra-root-canal states associated with the tooth having the corresponding root canal structure can be obtained by calculation using the specific resistance of the liquid.

If the intra-root-canal impedance values in various intra-root-canal states can be obtained, current values flowing in the root canal, voltage values across the intra-root-canal impedance values, and phase differences between the power supply and the measured voltage values and current values can be obtained by calculation or simulation. Electrical characteristic values of the model tooth 24' which constitute a model tooth data group can be theoretically obtained by using these values.

In the above calculation or simulation, a root canal having a cylindrical shape with a constant root canal diameter is assumed first. In this case, a resistance is proportional to the distance from the root apex position. When the root canal has a conical shape, the resistance exhibits a characteristic like a quadratic curve as a function of the distance from the root apex position.

The specific resistance of resistivity changes depending on the environment in the root canal. The specific resistance in each environment in the root canal and the root canal structure pattern are stored in the storage unit. Root apex position model data or intra-root-canal-position-specific model data can be calculated on the basis of these data.

For example, intra-root-canal-position-specific model data at each point before each root apex position is stored. It is determined, on the basis of changes in the intra-root-canal-position-specific model data, whether the data is data of a characteristic corresponding to a constant root canal diameter or data exhibiting a change in the diameter of the root canal in a conical shape. It is predicted, on the basis of the determined result, that the intra-root-canal-position-specific model data will change along a specific curve to the next point. The intra-root-canal-position-specific model data at that point is then predicted on the basis of the prediction. A measured data at the next point is compared with the predicted intra-root-canal-position-specific model data, and their difference is corrected to obtain the intra-root-canal-position-specific model data, thereby minimizing the error.

The fifth embodiment will be described. The fifth embodiment is associated with the above improvement of the second embodiment, and is directed to detect more precisely how the distal end of a measurement electrode 10 approaches a root apex position 23.

Figure 5:
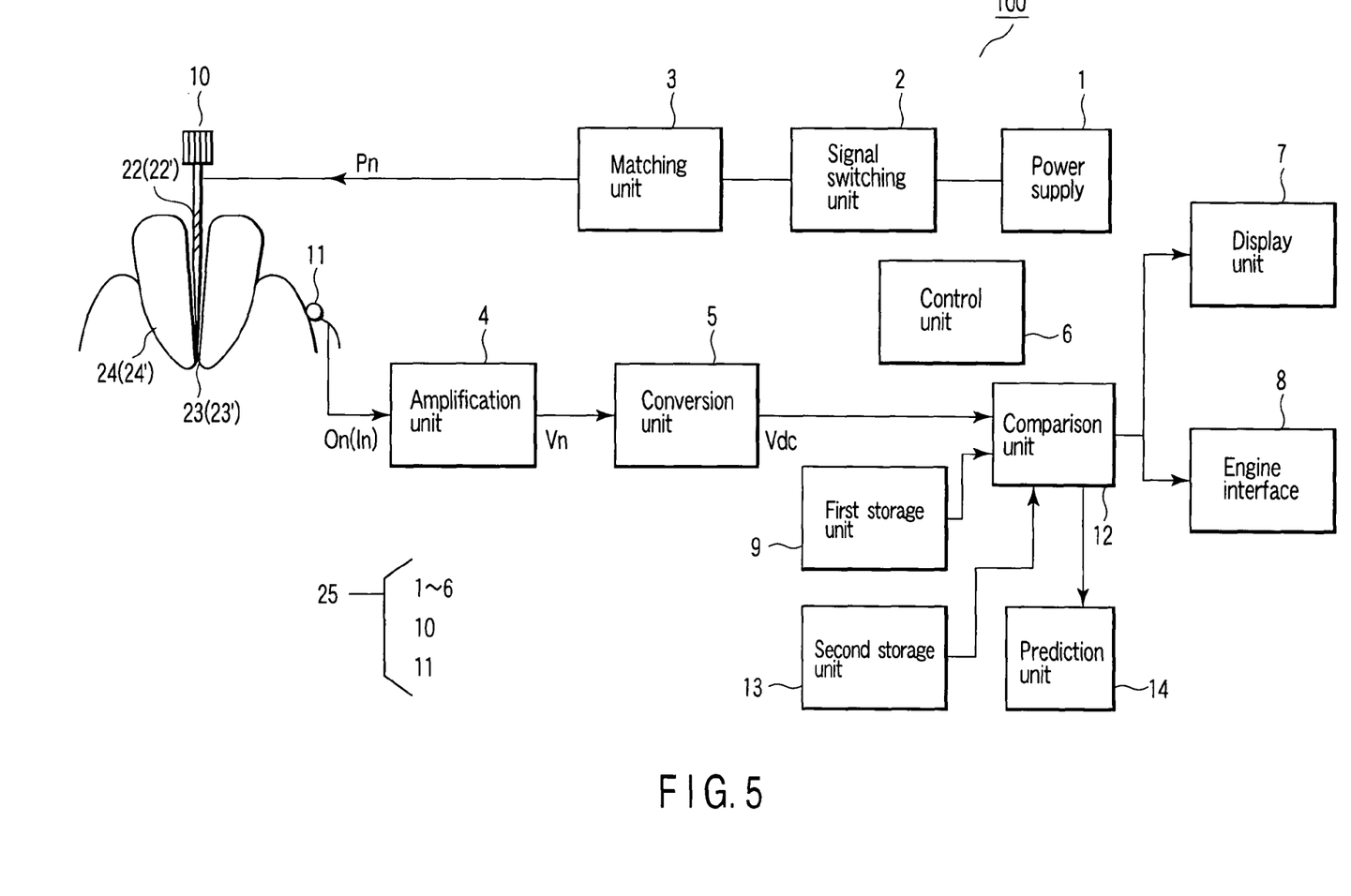
FIG. 5 is a view for explaining an apparatus according to the fifth embodiment of the invention of the present application.

Referring to FIG. 5, the power supply 1 outputs a plurality of types of measurement signals Pn. As the measurement signals Pn, signals of two different frequencies, e.g., 500 Hz and 2 kHz, can be used. The measurement signals Pn may be signals of three or more different frequencies. The measurement signals Pn may be signals which differ from each other in at least frequency, waveform, or peak value. In the invention of the present application, it is necessary to detect a plurality of types of electrical characteristic values between a measurement electrode 10 and a mouth electrode 11 on the basis of a plurality of types of measurement signals Pn, and the types of these signals can be selected on the basis of the principle of the invention of the present application to be described below.

Although the measurement signal Pn is applied to the measurement electrode 10, the signal may be applied to the mouth electrode 11.

For the sake of a more detailed description of this embodiment, this embodiment will exemplify a case wherein signals of two different frequencies, namely 500 Hz and 2 kHz, are used as the measurement signals Pn, and the measurement signals are applied to the measurement electrode. However, the invention of the present application is not limited to this case.

A power supply 1 outputs measurement signals of two different frequencies, namely 500 Hz and 2 kHz.

A signal switching unit 2 sequentially supplies the measurement signals of the two different frequencies, i.e., 500 Hz and 2 kHz, output from the power supply 1 to the measurement electrode under the control of a control unit 6. As the signal switching unit 2, a switching unit such as a so-called multiplexer or the like can be used.

A matching unit 3 is a portion which converts a signal from the signal switching unit into a signal with a voltage level at which the signal can be safely applied to the human body, and prevents a measurement current from needlessly flowing in the human body. The matching unit 3 adjusts the measurement signals Pn from the power supply 1 to signals suitable for being supplied to the measurement electrode 10. If, however, the measurement signals Pn from the power supply are signals suitable for being applied to the measurement electrode 10, the matching unit 3 can be omitted. In this embodiment, the matching unit 3 adjusts the measurement signals Pn of the two different frequencies, i.e., 500 Hz and 2 kHz, to a predetermined voltage value Vn.

An amplification unit 4 connected to the mouth electrode 11 amplifies a measured signal Qn output from the mouth electrode 11. The measured signal Qn is a value associated with an electrical characteristic value between the measurement electrode 10 and the mouth electrode 11. The electrical characteristic value can be any one of a current value In flowing between the two electrodes (to be referred to as a "measured current value In" hereinafter), a voltage value Vn between the two electrodes (to be referred to as the "measured voltage value Vn" hereinafter), a phase difference between the current value In and the measurement signal Pn, a phase difference between the voltage value Vn and the measurement signal Pn, and an impedance value Zn between the two electrodes (to be referred to as an "intra-root-canal impedance Zn" hereinafter), or a combination of these tooth data groups.

These electrical characteristic values can also be obtained from the measured signal Qn itself or by combining it with other signal values.

An electrical characteristic value in the invention of the present application is not limited to the measured current In. For the sake of a more detailed description of this embodiment, however, a case wherein the electrical characteristic value is the measured current In will be described.

The amplification unit 4 converts the measured current In into a voltage and amplifies the voltage, and a known amplifier can be used.

A conversion unit 5 is a circuit which converts the measured AC voltage Vn amplified by the amplification unit 4 into a DC voltage Vdc which can be read and stored by the control unit.

The control unit 6 controls predetermined devices in a root apex position detection apparatus 100 according to the embodiment.

Intra-root-canal-position-specific model data are stored in a first storage unit 9. The intra-root-canal-position-specific model data can be stored as it is or upon being converted into mathematical expressions or graphs. In this case, the intra-root-canal-position-specific model data are data having electrical characteristic values between the measurement electrode and the mouth electrode while the distal end of the measurement electrode 10 is located at a plurality of predetermined positions in a root canal 22' of a model tooth 24'. The larger the number of model teeth 24', the better.

Figure 6:
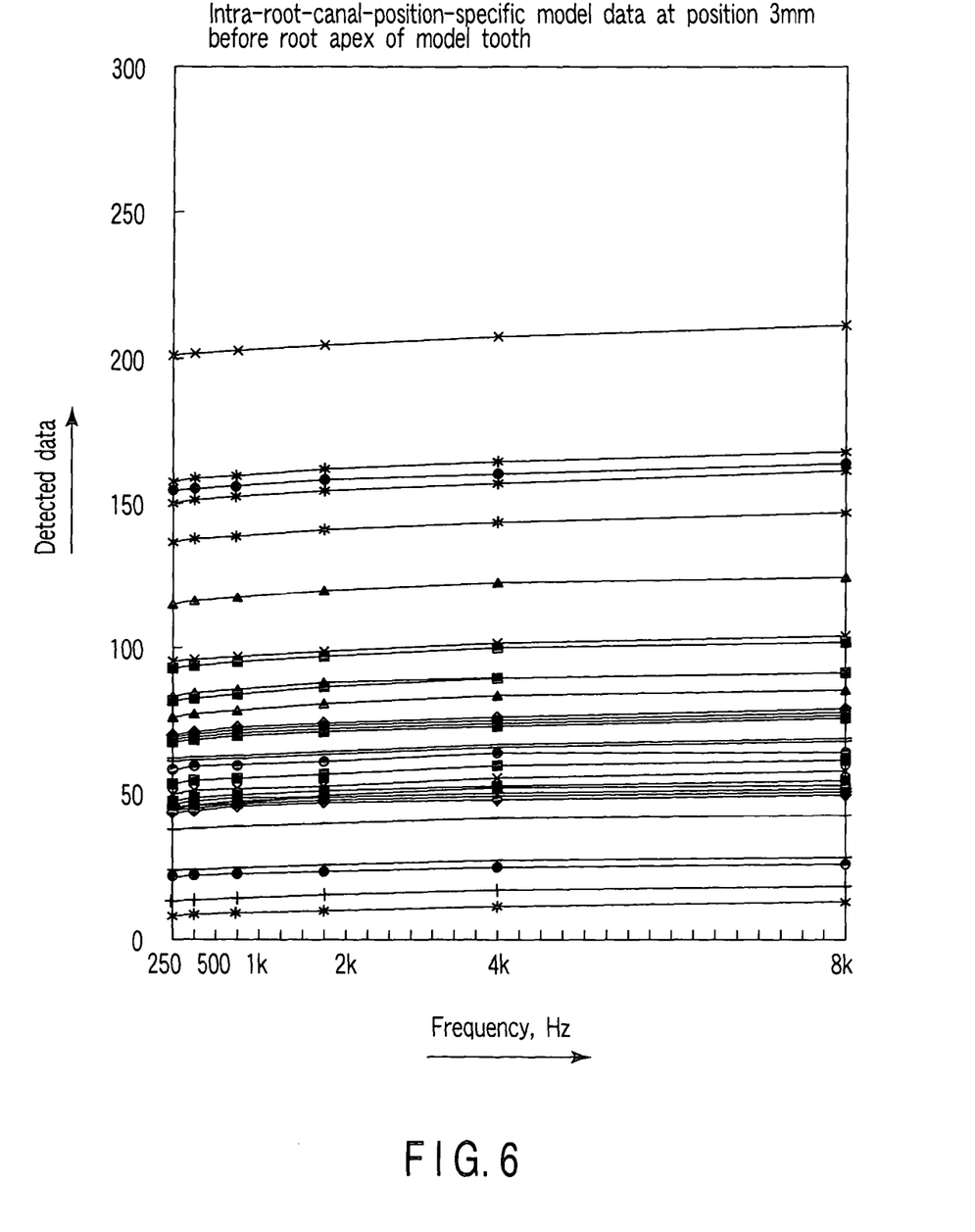
FIG. 6 is a graph showing a relation between the frequencies of measurement signals applied to the measurement electrode at a position 1 mm before the root apex position of each of a plurality of model teeth and the measured data of current value flowing between the measurement electrode and the mouth electrode caused by the measurement signals.
Figure 7:
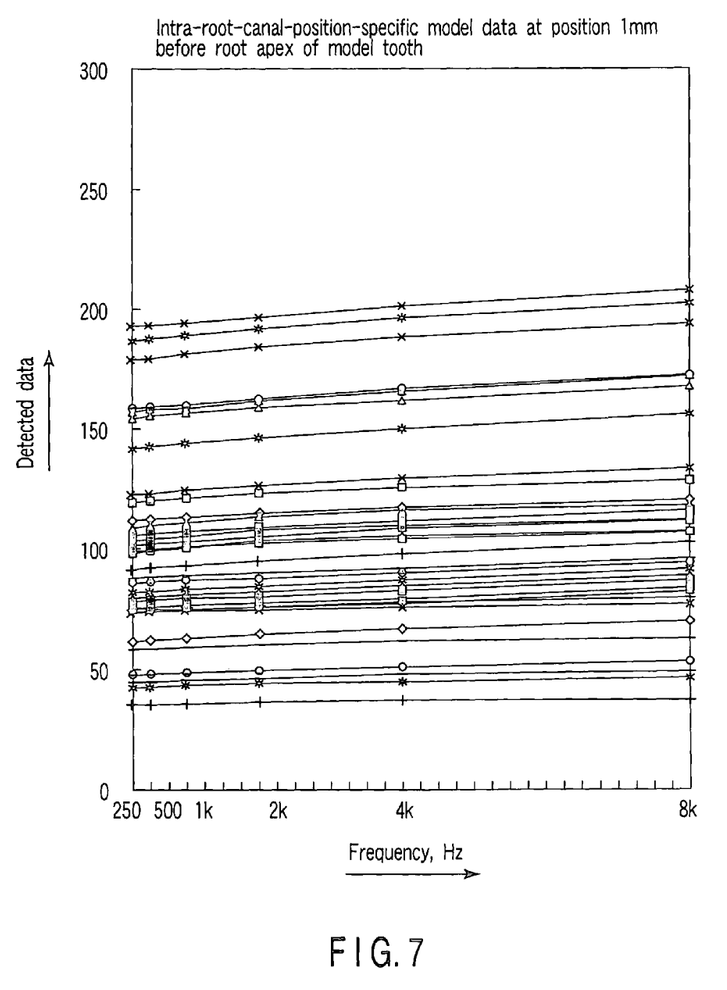
FIG. 7 is a graph showing a relation between the frequencies of the measurement signals applied to the measurement electrode at a position 3 mm before the root apex position of each of a plurality of model teeth and the measured data of current values flowing between the measurement electrode and the mouth electrode caused by the measurement signals.

FIGS. 6 and 7 show the intra-root-canal-position-specific model data associated with the model teeth 24' as in FIG. 2.

Referring to each graph, the ordinate represents the (quantified) measured current In; and the abscissa, the frequency of a measurement signal. FIG. 6 shows a relationship between the measured current In and a frequency f in a state wherein the distal end of the measurement electrode 10 is located 3 mm before the root apex position. FIG. 7 shows a relationship between the measured current In and the frequency f in a state wherein the distal end of the measurement electrode 10 is located 1 mm before the root apex position.

Referring to FIGS. 6 and 7, one line represents data associated with one model tooth 24'. In this case, even one model tooth 24' having the same root canal structure is considered as a different model tooth 24' if the state inside the root canal (e.g., the degree of a dry state or wet state or a change in thickness) differs.

This measured data was obtained by using Justy II (trade name) available from Toei Electric Co., Ltd as a root apex position detection apparatus upon partly modifying it. With this modification, the frequencies of measurement signals of 500 Hz and 2,000 Hz could be set in the range of 250 to 8,000 Hz. The output current of a detection output from the Justy II was supplied to a detection resistor, and the voltage across the resistor was used as measured data.

FIGS. 6 and 7 show the measured data of the model teeth 24' in a plurality of cases. In FIGS. 6 and 7, when perpendiculars are dropped at the positions of frequencies of 500 Hz and 2 kHz, the model tooth data group with the value of the intersection of each perpendicular and measured data for each model tooth 24' can be obtained. Referring to FIGS. 6 and 7, the model tooth data groups of the values of the intersections associated with the model teeth 24' in about 50 cases at the positions 3 mm and 1 mm before the root apex can be obtained. The data indicated values at 500 Hz indicate about 70 to 280 changes. These intra-root-canal-position-specific model data are stored in the first storage unit.

It can be understood from FIGS. 2, 6 and 7 that the ordinate data (electrical characteristic values) of the model tooth 24' at the root apex position and the positions 3 mm and 1 mm before the root apex position do not exhibit constant values. That is, the respective teeth have unique electrical characteristic values which are different from each other.

The intra-root-canal-position-specific model data are data associated with electrical characteristic values Rn between the measurement electrode 10 and the mouth electrode 11 at each distance from the measurement electrode 10 to a root apex position 23' in the process of the measurement electrode 10 being inserted into the root canal 22' toward the root apex position 23'.

A comparison unit 12 in the fifth embodiment can have a first function for detecting a root apex position the same as in the first embodiment. In addition to this function, the fifth embodiment can have a second function or/and third function of outputting a test result (position information) indicating how far the distal end of the measurement electrode 10 is away from the root apex position.

The second function will be described below. The second function is the same as the above second embodiment. That is, in FIG. 5, in the process of the distal end of the measurement electrode 10 being inserted into the root canal 22', the power supply 1 alternately supplies measurement signals of 500 Hz and 2 kHz to the measurement electrode 10. As a consequence, as the distal end of the measurement electrode 10 is inserted into the root canal 22', the electrical characteristic value Rn between the two electrodes changes.

The comparison unit 12 compares the changing electrical characteristic value Rn with the plurality of the intra-root-canal-position-specific model data stored in the first storage unit to detect an intra-root-canal-position-specific model data in a predetermined relationship. The comparison unit 12 detects to which position on the model tooth 24' the intra-root-canal-position-specific model data in the predetermined position corresponds, and outputs the detected result to a display unit 7. Making a display unit 7 display the detected result allows the dentist to accurately grasp how the measurement electrode 10 approaches the root apex position 23.

By generating the intra-root-canal-position-specific model data of the model tooth 24' at 1-mm intervals from the root apex position, the fifth embodiment can detect in a resolution of 1 mm how the distal end of the measurement electrode 10 approaches the root apex position 23'.

The third function will be described next. The third function is to more precisely detect how the distal end of the measurement electrode 10 approaches the root apex position 23. The third function detects and displays that the distal end of the measurement electrode is located at least one position anywhere between position a1 in the root canal 22' of the model tooth 24' and position a2 ahead of the point a1.

Figure 8:
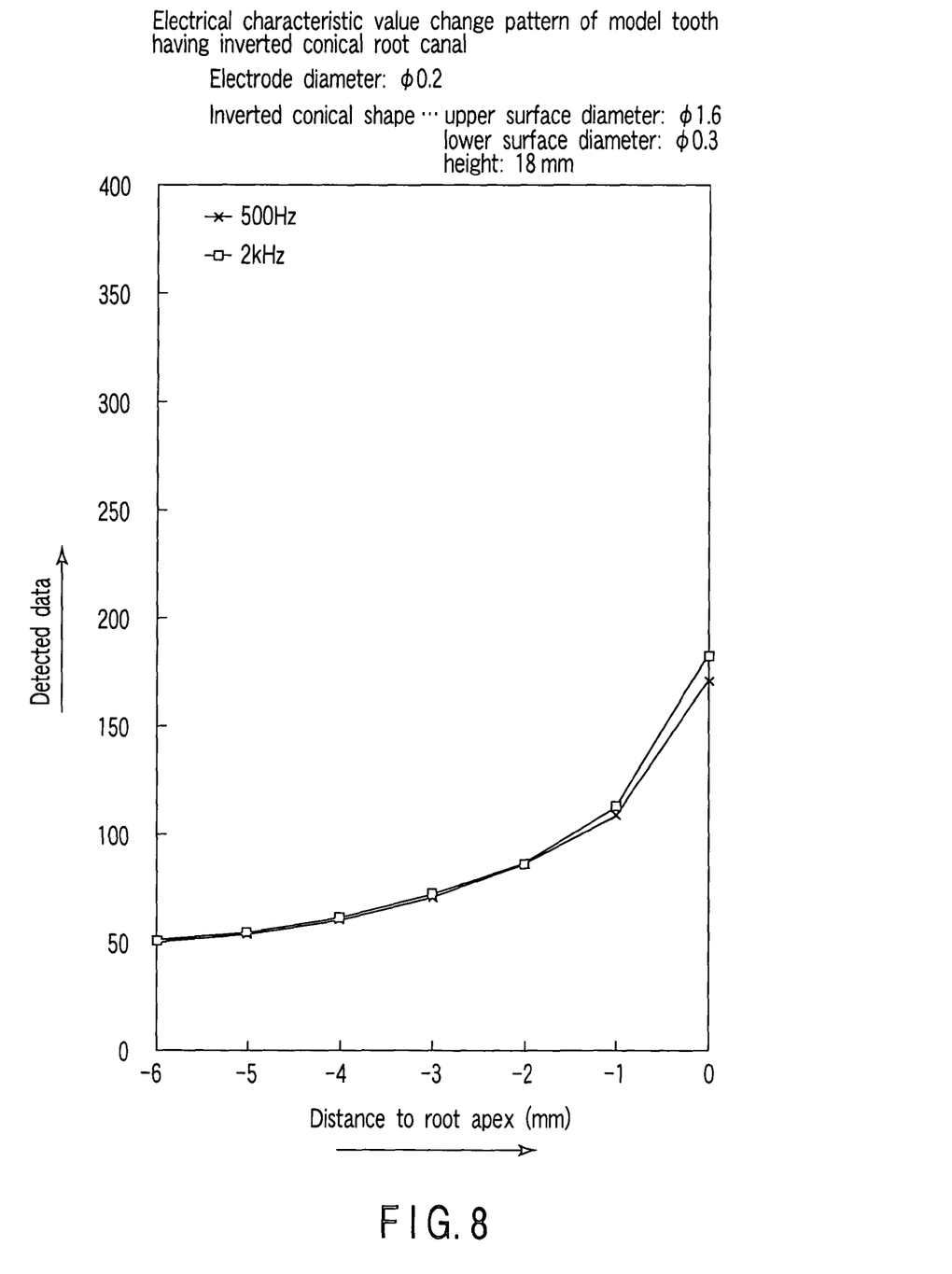
FIG. 8 is a graph showing electrical characteristic value change patterns of a model tooth having an inverted conical root canal.
Figure 9:
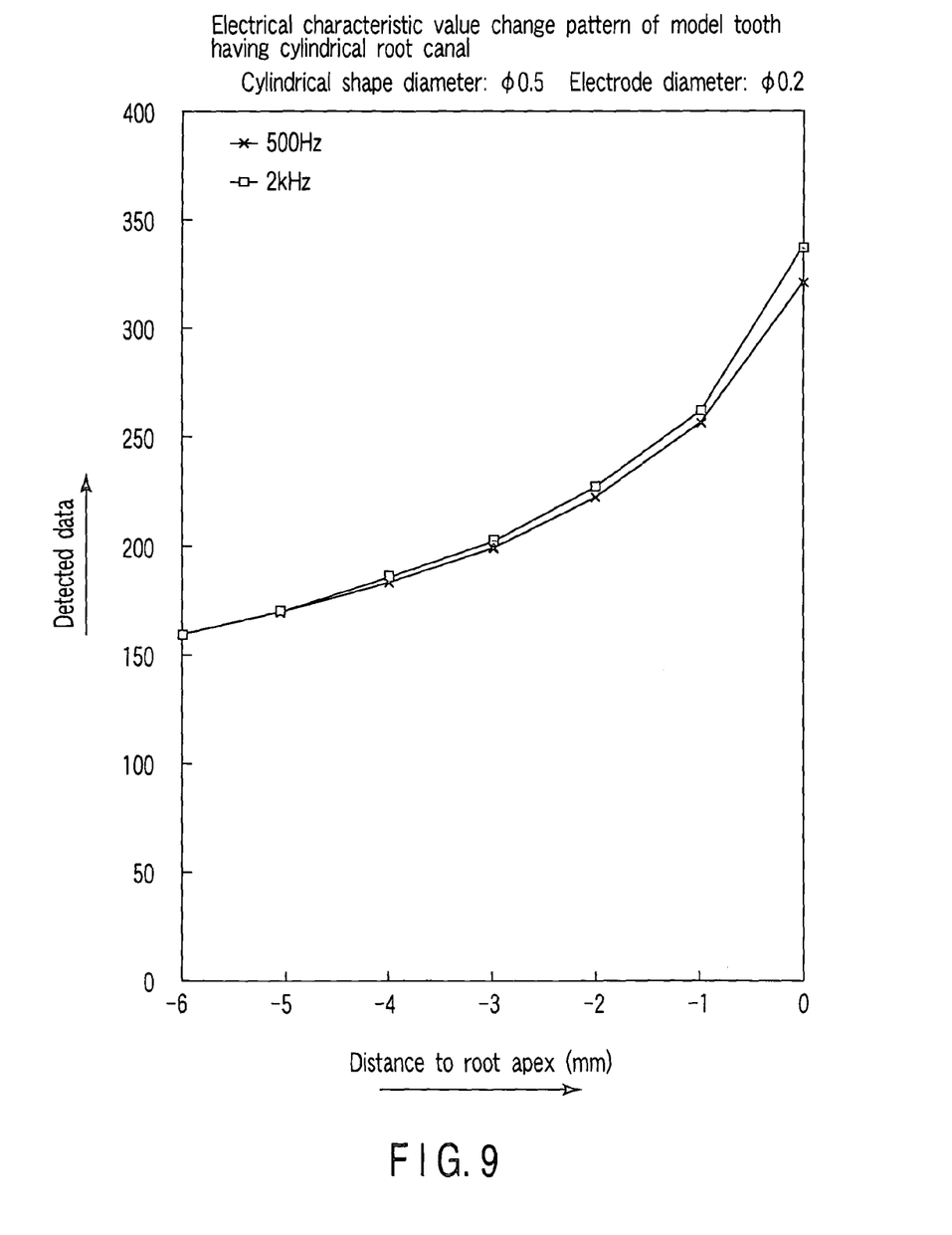
FIG. 9 is a graph showing electrical characteristic value change patterns of a model tooth having a cylindrical root canal.

The third function can use an electrical characteristic value change pattern of a test tooth. FIGS. 8 and 9 show examples of electrical characteristic value change patterns of a test tooth. For a model tooth 24' whose root canal 22' has an inverted conical shape, FIG. 8 shows the change pattern of the electrical characteristic value between the measurement electrode 10 and the mouth electrode 11 as the measurement electrode having a diameter of 0.2 mm is inserted from the root canal orifice into the root canal 22' of the model tooth 24'.

Likewise, for a model tooth 24' whose root canal 22' has a cylindrical shape, FIG. 9 shows the change pattern of the electrical characteristic value between the measurement electrode 10 and mouth electrode 11 as the measurement electrode having a diameter of 0.2 mm is inserted from the root canal orifice into the root canal 22' of the model tooth 24'.

The third function will be described in a case wherein the comparison unit 12 shown in FIG. 5 detects that the distal end of the measurement electrode 10 has reached a position 3 mm before the root apex, by detecting that the electrical characteristic value between the mouth electrode 11 and the measurement electrode 10 inserted into a root canal 22 of a test tooth 24 coincides with one of the intra-root-canal-position-specific model data shown in FIG. 6 on the basis of the second function.

The third function uses predictive data processed by a prediction unit 14 shown in FIG. 5. That is, it is grasped, on the basis of a change pattern obtained until the distal end of the measurement electrode 10 reaches the position 3 mm before the root apex, that the test tooth 24 has an inverted conical intra-root-canal structure. Upon reception of this result, the prediction unit 14 grasps, in the data shown in FIG. 8, that detected data corresponding to each of the measurement signals of 500 Hz and 2 kHz which is obtained until the measurement electrode reaches the position 1 mm before the root apex increases at the same change rate as that of a predetermined inverted conical pattern.

When the distal end of the measurement electrode 10 reaches the position 3 mm before the root apex, the prediction unit 14 predicts an electrical characteristic value (i.e., detected data) (to be respectively referred to as a "predicted electrical characteristic value" and "predicted detected data" hereinafter) when the distal end of the measurement electrode 10 reaches the position 1 mm before the root apex, on the basis of a measured electrical characteristic value (i.e., detected data) (to be respectively referred to as a "measured electrical characteristic value" and "measured detected data" hereinafter) and the increase at the position 1 mm before the root apex which is graphed from FIG. 8.

On the basis of these measured detected data and predicted detected data, the comparison unit 12 predicts intra-root-canal-position-specific model data at smaller intervals between the position 3 mm from the root apex and the position 1 mm before the root apex. This prediction can be executed by a method of linearly approximating the interval between the position 3 mm before the root apex and the position 1 mm before the root apex and dividing the interval into a plurality of equal parts (e.g., 10 or 20 parts).

The predictive intra-root-canal-position-specific model data predicted and fractionalized in this manner are stored in a second storage unit. Although the second storage unit may be a storage mechanism different from the first storage unit, the two storage units may be realized by the same storage mechanism.

In the process of the distal end of the measurement electrode 10 being inserted into the root canal 22 of the test tooth 24, the power supply 1 supplies measurement signals of 500 Hz and 2 kHz to the measurement electrode 10. As a result, as the distal end of the measurement electrode 10 is inserted into the root canal 22, the electrical characteristic value Rn between the two electrodes changes.

The comparison unit 12 compares the changing electrical characteristic values (i.e., the two types of measured electrical characteristic values Rn with respect to the measurement signals of 500 Hz and 2 kHz) with the intra-root-canal-position-specific model data stored in the first storage unit and the predictive intra-root-canal-position-specific model data stored in the second storage unit. When it is detected that an intra-root-canal-position-specific model data stored in the first and second storage units include data in a predetermined relationship with the measurement electrical characteristic values, the comparison unit 12 checks to which position in the root canal the data in the predetermined relationship correspond, and outputs the position as a positional information to the display unit 7. Display on the display unit 7 then allows the dentist to precisely grasp how the root apex position 23 approaches the root apex position 23.

The fifth embodiment uses intra-root-canal-position-specific model data at the positions 3 mm and 1 mm before the root apex. However, the embodiment can use an intra-root-canal-position-specific model data obtained at smaller intervals (1-mm intervals).

By using predictive electrical characteristic values predicted and fractionalized by the prediction unit in this manner, the position of the distal end of the measurement electrode 10 can be detected more precisely.

According to an embodiment of the invention of the present application, a root apex position can be detected accurately.

According to an embodiment of the invention of the present application, a root apex position can be measured more accurately by reducing the influence of the state of the root canal.

According to an embodiment of the invention of the present application, the distance of the distal end of the measurement electrode from the root apex position can be measured precisely.

According an embodiment of the invention of the present application, the root canal can be enlarged accurately and easily.

According to an embodiment of the invention of the present application, the operation time for enlarging the root canal can be shortened.

According to an embodiment of the invention of the present application, it is not necessary to perform the operation of fixing a silicone stopper to the measurement electrode, which is required to finish the operation of the measurement electrode before the root apex.

What is claimed is:

1. A root apex position detection apparatus for detecting a root apex position of a root canal of a test tooth, comprising:
   a measurement electrode which is configured for insertion into the root canal;
   a mouth electrode which is configured for placement on an intraoral surface;
   a power supply which applies a plurality of types of measurement signals to one of the measurement electrode and the mouth electrode;
   a storage unit to store root apex position model data, intra-root-canal-position-specific model data, and predictive intra-root-canal-position-specific model data, (1) the root apex position model data having a plurality of model tooth data groups, each of the model tooth data groups comprising a plurality of impedance values between the measurement electrode and the mouth electrode with respect to each of the plurality of types of measurement signals while a distal end of the measurement electrode is placed at a root apex position of each model tooth, (2) the intra-root-canal-position-specific model data comprising a plurality of model tooth data groups, each of the model tooth data groups comprising a plurality of impedance values between the measurement electrode and the mouth electrode with respect to a plurality of types of measurement signals in a state in which the distal end of the measurement electrode is located at each of a plurality of predetermined positions in each of the model teeth, and (3) the predictive intra-root-canal-position-specific model data comprising a plurality of groups having impedance values predicted at a position midway between one predetermined position of a plurality of predetermined positions and the next predetermined position, and the model tooth including different model teeth for each model tooth data group;
   a signal switching unit to sequentially supply the plurality of types of measurement signals to one of the measurement electrode and the mouth electrode;
   a detection unit which sequentially detects a plurality of impedance values between the measurement electrode and the mouth electrode with respect to each of the plurality of types of measurement signals, in the process of inserting the measurement electrode into the root canal toward the root apex position, while sequentially applying each of the plurality of types of measurement signals to one of the measurement electrode and the mouth electrode;
   a comparison unit which compares each test tooth data group comprising the plurality of impedance values sequentially detected by the detection unit with each of the groups in the root apex position model data, intra-root-canal-position-specific model data, and predictive intra-root-canal-position-specific model data stored in the storage unit, detects that there is a group in a predetermined relationship with the test tooth data group, and outputs a detected result; and
   a display unit to display the detected result output from the comparison unit.

2. A root apex position detection apparatus according to claim 1, further comprising a prediction unit which predicts an impedance value at a position midway between an intra-root-canal position indicated by the detected result output from the comparison unit and the root apex position,
   wherein the impedance value predicted by the prediction unit is used as the intra-root-canal-position-specific model data.

* * * * *